(12) United States Patent
Pepin

(10) Patent No.: US 6,652,507 B2
(45) Date of Patent: Nov. 25, 2003

(54) INTRAVASCULAR CATHETER HAVING MULTI-LAYERED TIP

(75) Inventor: Henry J. Pepin, Loretto, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 29 days.

(21) Appl. No.: 09/898,742

(22) Filed: Jul. 3, 2001

(65) Prior Publication Data

US 2003/0009150 A1 Jan. 9, 2003

(51) Int. Cl.[7] ............................................. A61M 25/00
(52) U.S. Cl. ..................... 604/523; 604/529; 604/528; 604/264
(58) Field of Search ................................. 604/523, 528, 604/529, 525, 264, 526, 527, 534

(56) References Cited

U.S. PATENT DOCUMENTS

| | | | |
|---|---|---|---|
| 4,385,635 A | 5/1983 | Ruiz | 128/658 |
| 4,464,176 A | 8/1984 | Wijayarathna | 604/164 |
| 4,531,943 A | 7/1985 | Van Tassel et al. | 604/280 |
| 4,563,181 A | 1/1986 | Wijayarathna et al. | 604/280 |
| 4,571,240 A | 2/1986 | Samson et al. | 604/96 |
| 4,596,563 A | 6/1986 | Pande | 604/264 |
| 4,636,346 A | 1/1987 | Gold et al. | 264/139 |
| 4,665,604 A | 5/1987 | Dubowik | 29/415 |
| 4,739,768 A | 4/1988 | Engelson | 128/658 |
| 4,753,765 A | 6/1988 | Pande | 264/149 |
| 4,801,297 A | 1/1989 | Mueller | 604/280 |
| 4,841,976 A | 6/1989 | Packard et al. | 128/657 |
| 4,842,590 A | 6/1989 | Tanabe et al. | 604/282 |
| 4,863,442 A | 9/1989 | DeMello et al. | 604/282 |
| 4,886,506 A | 12/1989 | Lovgren et al. | 604/280 |
| 5,017,259 A | 5/1991 | Kohsai | 156/294 |
| 5,061,257 A | 10/1991 | Martinez et al. | 604/282 |
| 5,078,702 A | 1/1992 | Pomeranz | 604/280 |

(List continued on next page.)

FOREIGN PATENT DOCUMENTS

| | | |
|---|---|---|
| EP | 0 452 123 B1 | 10/1991 |
| WO | WO 98/42268 | 10/1998 |

Primary Examiner—Ira S. Lazarus
Assistant Examiner—Camtu Nguyen
(74) Attorney, Agent, or Firm—Crompton, Seager & Tufte, LLC

(57) ABSTRACT

An intravascular catheter having a multi-layered distal tip including an inner layer, an intermediate layer and an outer layer wherein the intermediate layer is formed of a polymeric material loaded with a high percentage of radiopaque agent, and the inner and outer layers are formed of readily bondable materials which substantially cover the intermediate layer to thereby increase surface area contact and bond strength therebetween.

25 Claims, 2 Drawing Sheets

U.S. PATENT DOCUMENTS

| | | | | |
|---|---|---|---|---|
| 5,085,649 A | | 2/1992 | Flynn | 604/282 |
| 5,171,232 A | | 12/1992 | Castillo et al. | |
| 5,221,270 A | | 6/1993 | Parker | 604/282 |
| 5,231,994 A | | 8/1993 | Harmjanz | 128/772 |
| 5,234,416 A | | 8/1993 | Macaulay et al. | 604/282 |
| 5,240,004 A | * | 8/1993 | Walinsky et al. | 128/662.06 |
| 5,254,107 A | | 10/1993 | Soltesz | 604/282 |
| 5,281,677 A | * | 1/1994 | Onwunaka et al. | 525/458 |
| 5,368,048 A | | 11/1994 | Stoy et al. | 128/772 |
| 5,447,503 A | | 9/1995 | Miller | 604/280 |
| 5,509,910 A | | 4/1996 | Lunn | 604/282 |
| 5,531,721 A | | 7/1996 | Pepin et al. | 604/282 |
| 5,545,149 A | | 8/1996 | Brin et al. | 604/265 |
| 5,571,073 A | | 11/1996 | Castillo | 604/282 |
| 5,584,821 A | | 12/1996 | Hobbs et al. | 604/280 |
| 5,599,319 A | | 2/1997 | Stevens | 604/264 |
| 5,676,659 A | | 10/1997 | McGurk | 604/282 |
| 5,762,637 A | | 6/1998 | Berg et al. | 604/264 |
| 5,769,830 A | | 6/1998 | Parker | 604/282 |
| 5,792,124 A | | 8/1998 | Horrigan et al. | 604/282 |
| 5,820,612 A | | 10/1998 | Berg | 604/282 |
| 5,843,051 A | | 12/1998 | Adams et al. | 604/280 |
| 5,846,199 A | | 12/1998 | Hijlkema et al. | 600/435 |
| 5,908,413 A | * | 6/1999 | Lange et al. | 604/529 |
| 5,911,715 A | | 6/1999 | Berg et al. | 604/525 |
| 5,938,653 A | | 8/1999 | Pepin | 604/527 |
| 5,948,489 A | * | 9/1999 | Hopkins | 428/34.9 |
| 6,077,258 A | | 6/2000 | Lange et al. | |
| 6,090,099 A | * | 7/2000 | Samson et al. | 604/527 |
| 6,106,510 A | * | 8/2000 | Lunn et al. | 604/525 |
| 6,165,166 A | * | 12/2000 | Samuelson et al. | 504/524 |
| 6,171,295 B1 | * | 1/2001 | Garabedian et al. | 604/524 |
| 6,171,297 B1 | * | 1/2001 | Pedersen et al. | 604/527 |
| 6,210,396 B1 | * | 4/2001 | MacDonald et al. | 604/529 |
| 2001/0003297 A1 | | 6/2001 | Pedersen et al. | |
| 2001/0051790 A1 | * | 12/2001 | Parker | 604/103.01 |
| 2002/0156460 A1 | * | 10/2002 | Ye et al. | 604/534 |

* cited by examiner

INTRAVASCULAR CATHETER HAVING MULTI-LAYERED TIP

FIELD OF THE INVENTION

The present invention generally relates to intravascular catheters. More specifically, the present invention relates to intravascular catheters such as guide and diagnostic catheters having multi-layered tips.

BACKGROUND OF THE INVENTION

Diagnostic catheters and guide catheters are commonly used to facilitate the diagnosis and treatment of vascular diseases such as coronary artery disease and peripheral vascular disease. Because intravascular catheters must be navigated through a patient's vascular system, it is desirable that the distal tip be atraumatic to avoid damaging the vascular wall, and radiopaque to facilitate radiographic visualization. However, soft polymer tips loaded with radiopaque material are sometimes difficult to bond to the shaft and sometimes have visual defects due to migration of the radiopaque material to the surface of the polymer tip.

SUMMARY OF THE INVENTION

To address these problems, the present invention provides, in one example, an intravascular catheter having a multi-layered distal tip including an inner layer, an intermediate layer and an outer layer wherein the intermediate layer is formed of a polymeric material loaded with a high percentage of radiopaque agent, and the inner and outer layers are formed of readily bondable materials which substantially cover the intermediate layer to thereby increase surface area contact and bond strength therebetween.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
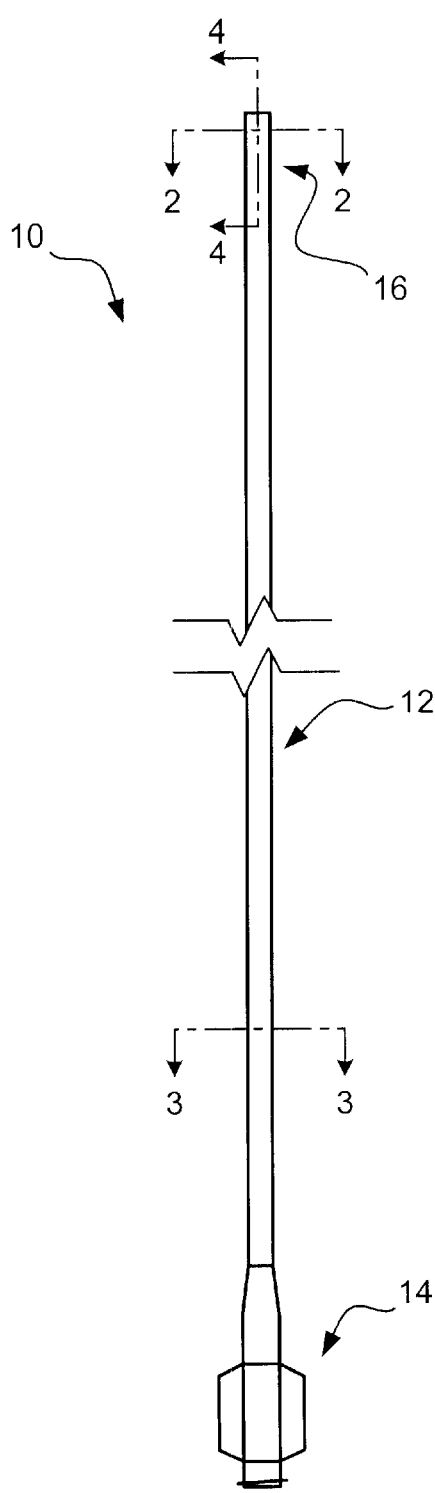
FIG. 1 is a plan view of an intravascular catheter in accordance with an embodiment of the present invention, shown as a guide or diagnostic catheter.

Refer now to FIG. 1 which illustrates an intravascular catheter 10 in accordance with an embodiment of the present invention. For purposes of illustration and discussion only, the intravascular catheter 10 is shown in the form of a guide or diagnostic catheter, but may comprise virtually any catheter used for intravascular applications. The intravascular catheter 10 has a length and an outside diameter sufficient to enable intravascular insertion and navigation. For example, the catheter 10 may have a length of approximately 100 cm–150 cm and an outside diameter of approximately 4F-9F.

The intravascular catheter 10 includes an elongate shaft 12 having a proximal end and distal end. A distal tip 16 is connected to the distal end of the elongate shaft 12. The distal tip 16 and a distal portion of the elongate shaft 12 may be curved depending on the particular clinical application. The elongate shaft 12 and the distal tip 16 include a lumen 18 extending therethrough to facilitate insertion of other medical devices (e.g., guide wires, balloon catheters, etc.) therethrough, and/or to facilitate injection of fluids (e.g. radiopaque dye, saline, drugs, etc.) therethrough. A conventional manifold 14 is connected to the proximal end of the elongate shaft 12 to facilitate connection to other medical devices (e.g., syringe, Y-adapter, etc.) and to provide access to the lumen 18.

Figure 3:
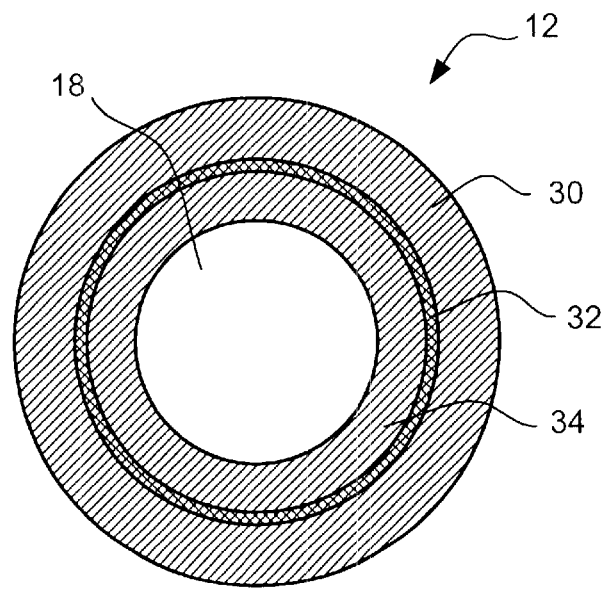
FIG. 3 is a cross-sectional view taken along line 3—3 in FIG. 1.
Figure 4A:
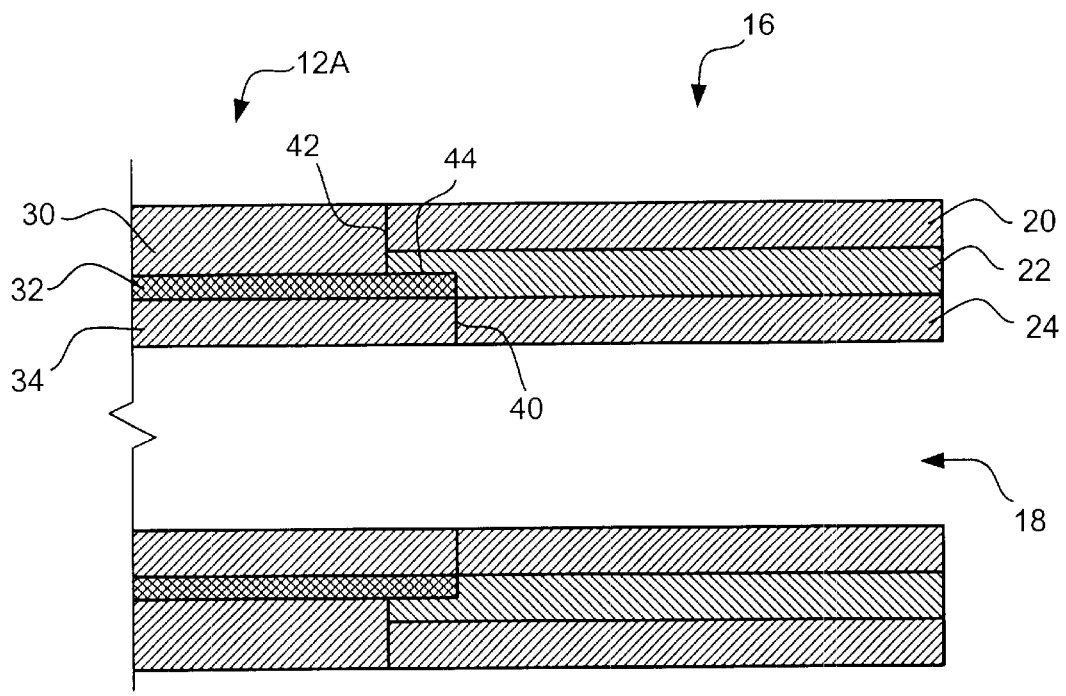
FIG. 4A is a longitudinal sectional view taken along line 4—4 in FIG. 1, showing a multi-layer shaft.
Figure 4B:
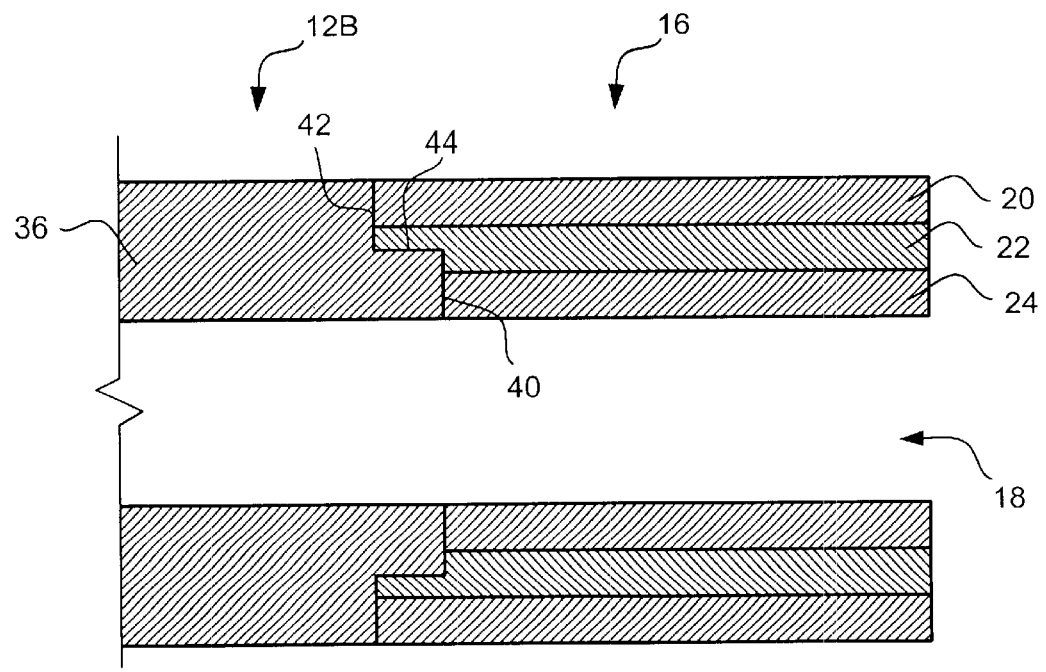
FIG. 4B is a longitudinal sectional view taken along line 4—4 in FIG. 1 showing a uni-layer shaft.

As best seen in FIGS. 3, 4A and 4B, the elongate shaft 12 may be multi-layered or uni-layered. A multi-layer elongate shaft 12A is illustrated in FIG. 4A, and a uni-layer shaft 12B is illustrated in FIG. 4B. The multi-layer elongate shaft 12A may include an outer layer 30, a reinforcement structure 32, and an inner layer 34. The uni-layer elongate shaft 12B may comprise a single polymer layer 36.

In the multi-layer embodiment illustrated in FIGS. 3 and 4A, the outer layer 30 may comprise a polymeric material such as polyether block amide having a hardness of 63 D and loaded with a radiopaque agent such as 30% bismuth subcarbonate. The reinforcement structure 32 may comprise a tubular braid of 304LV stainless steel wire. The inner layer 34 may comprise a polymeric material such as a polyether block amide having a hardness of 65 D and loaded with a radiopaque agent such as 40% bismuth subcarbonate. Alternatively, the inner layer 34 may comprise a blend of a 46% polyurethane elastomer having a hardness of 65 D and loaded with 20% barium sulfate and 54% polyether block amide having a hardness of 67 D and loaded with 40% bismuth subcarbonate. In the uni-layer embodiment illustrated in FIG. 4B, the single layer 36 may comprise a polymeric material such as a polyether block amide having a hardness of 72 D and loaded with a radiopaque agent such as 30% bismuth subcarbonate.

The outer layer 30 may have an outside diameter of approximately 0.067 inches and an inside diameter of approximately 0.057 inches. The braid reinforcement structure 32 may have a diametric center point of approximately 0.055 to 0.057 inches. The inner layer 34 may have an inside diameter of approximately 0.045 inches and an outside diameter of approximately 0.055 inches.

Polyether block amide polymers are commercially available under the trade name Pebax®. Pebax brand polyether block amide polymers are available in a variety of durometers which may be utilized individually or combined to obtain the desired hardness. Polyurethane elastomers are commercially available from the Dow Chemcial Company under the trade name Pellethane®. Those skilled in the art will recognize that the dimensions and materials described with reference to the elongate shaft 12 may be varied depending on the particular clinical application and the desired performance characteristics.

Figure 2:
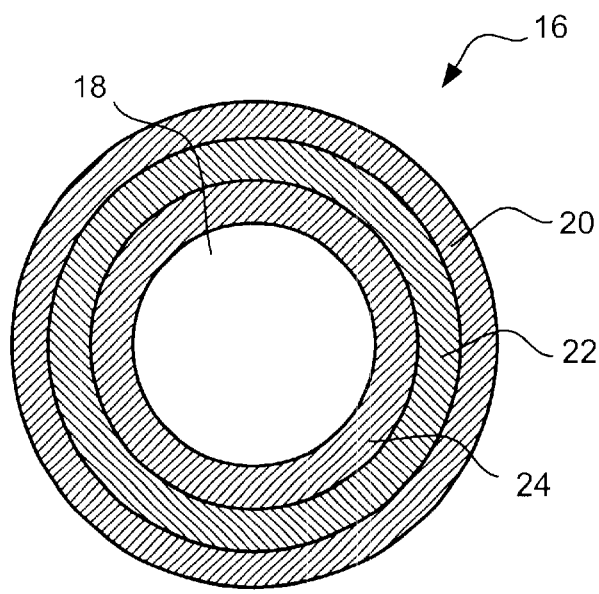
FIG. 2 is a cross-sectional view taken along line 2—2 in FIG. 1.

As best seen in FIGS. 2, 4A and 4B, the distal tip 16 includes an outer layer 20, an intermediate layer 22 and an inner layer 24. The intermediate layer 22 may be formed of a polymeric material that is not readily bondable, such as a lubricious polymer or a polymeric material that is rendered less bondable, as with a polymer loaded with a high percentage of radiopaque agent. Examples of materials that are not readily bondable include PTFE, HDPD, LDPE, and other polymer materials with lubricous qualities. In the context of a highly loaded polymeric material, the intermediate layer 22 may comprise, for example, polyether block amide having a hardness of 55 D to 67 D and loaded with a high percentage of radiopaque agent such as tungsten. The intermediate layer 22 may be loaded (admixed and homogenously distributed) with more than 50%, and preferably more than 70%, radiopaque material (e.g., metal powder) to render the intermediate layer 22 highly radiopaque. Loading the intermediate layer 22 with a high percentage of radiopaque agent may compromise bondability and may cause visual defects due to the migration of radiopaque agent to the surface of the intermediate layer 22. To address these potential problems, the distal tip 16 utilizes a multi-layered construction including outer layer 20 and inner layer 24.

Preferably, the outer and inner layers 20/24 extend the full length of the intermediate layer 22 to maximize the surface area contact therebetween as best seen in FIGS. 4A and 4B. However, it is contemplated that the outer and inner layers 20/24 may extend a substantial length, but less than the full length of the intermediate layer 22 while still providing a significant increase in bond strength. The outer and inner layers 20/24 comprise structural elements which hold the intermediate layer 22 and which secure the distal tip 16 to the distal end of the elongate shaft 12. The structural characteristic of the outer and inner layers 20/24 provide tensile strength to the distal tip 16 and the connection to the shaft 12 such that the outer and inner layers 20/24, in addition to the intermediate layer 22, are well secured to the distal end of the elongate shaft 12.

The outer layer 20 and the inner layer 24 may comprise a polymeric material such as polyether block amide having a hardness of 47 D and loaded with a radiopaque agent such as 40% bismuth subcarbonate. Note that the polymer material of the outer layer 20 and the inner layer 24 may comprise the same material as the intermediate layer 22 to increase bond strength therebetween. The outer, intermediate and inner layers 20/22/24 may comprise a single co-extrusion, or may comprise individual tubular elements thermally welded together.

The outer layer 20 may have a wall thickness of 0.001 to 0.005 (preferably 0.003) inches and an outside diameter of approximately 0.078 to 0.084 (preferably 0.080) inches. The intermediate layer 22 may have a wall thickness of approximately 0.001 to 0.005 (preferably 0.003) inches and an outside diameter corresponding to the inside diameter of the outer layer 20. The inner layer 24 may have a wall thickness of approximately 0.001 to 0.005 (preferably 0.003) inches with an inside diameter of approximately 0.050 to 0.060 (preferably 0.056) inches and an outside diameter corresponding to the inside diameter of the intermediate layer 22.

Those skilled in the art will recognize that the dimensions and the materials described with reference to the outer, intermediate and inner layers 20/22/24 may be varied depending on the particular clinical application and the desired performance characteristics. For example, the materials of the outer, intermediate and inner layers 20/22/24 may comprise other relatively flexible and soft polymeric materials. In all instances, it is desirable that the polymeric materials forming the outer, intermediate and inner layers 20/22/24 comprise the same or similar polymeric material to facilitate strong adhesion therebetween.

The distal tip 16 is preferably thermally bonded to the distal end of the elongate shaft 12 to form a lap joint therebetween. The lap joint connection between the elongate shaft 12 and the distal tip 16 includes an inner vertical surface 40, a horizontal surface 44 and an outer vertical surface 42 as best seen in FIGS. 4A and 4B. The lap joint connection between the elongate shaft 12 and the distal tip 16 preferably does not alter the inside or outside diameters, thereby forming a smooth connection therebetween.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter, comprising:

an elongate shaft having a proximal end, a distal end and a lumen extending therethrough, the elongate shaft having a length and an outside diameter suitable for intravascular navigation; and a distal tip having a proximal end, a distal end and a lumen extending therethrough, the proximal end of the tip connected to the distal end of the elongate shaft, the distal end of the tip defining a terminal end of the catheter, wherein the distal tip includes an intermediate layer comprising a polymer including more than 50% radiopaque agent disposed between inner and outer polymeric layers, wherein the inner and outer polymeric layers increase bond strength between the intermediate layer and the distal end of the elongate shaft.

2. An intravascular catheter as in claim 1, wherein the intermediate layer of the distal tip comprises more than 70% radiopaque agent.

3. An intravascular catheter as in claim 1, wherein the radiopaque agent is homogeneously distributed throughout the polymer of the inner layer.

4. An intravascular catheter as in claim 1, wherein the inner and outer layers extend to the distal end of the distal tip.

5. An intravascular catheter as in claim 1, wherein the elongate shaft comprises a polymer which is the same as the polymer of the layers of the distal tip.

6. An intravascular catheter as in claim 1, wherein the inner, intermediate and outer layers of the distal tip are co-extruded.

7. An intravascular catheter as in claim 1, wherein the proximal end of the distal tip forms a lap joint with the distal end of the elongate shaft.

8. An intravascular catheter as in claim 7, wherein an inner diameter of the elongate shaft is equal to an inner diameter of the distal tip across the lap joint.

9. An intravascular catheter as in claim 8, wherein an outer diameter of the elongate shaft is equal to an outer diameter of the distal tip across the lap joint.

10. An intravascular catheter as in claim 1, wherein the radiopaque agent is admixed with the polymer of the inner layer.

11. An intravascular catheter as in claim 1, wherein the radiopaque agent comprises a metal powder.

12. An intravascular catheter, comprising:

an elongate shaft having a proximal end, a distal end and a lumen extending therethrough, the elongate shaft having a length and an outside diameter suitable for intravascular navigation; and a distal tip having a proximal end, a distal end and a lumen extending therethrough, the proximal end of the tip connected to the distal end of the elongate shaft, the distal end of the tip defining a terminal end of the catheter, wherein the distal tip includes an intermediate layer comprising a first polymer disposed between inner and outer layers comprising a second polymer, wherein the first polymer is inherently or rendered less bondable than the second polymer, wherein the first polymer comprises at least 50% radiopaque agent.

13. An intravascular catheter as in claim 12, wherein the polymer of the inner and outer layers of the distal tip are readily bondable.

14. An intravascular catheter as in claim 12, wherein the agent comprises a metal powder.

15. An intravascular catheter as in claim 12, wherein the inner and outer to the distal end of the distal tip.

16. An intravascular catheter as in claim 12, wherein the elongate shaft polymer which is the same as the polymer of the inner and outer layers of the distal tip.

17. An intravascular catheter as in claim 12, wherein the inner, intermediate and outer layers of the distal tip are co-extruded.

18. An intravascular catheter as in claim 12, wherein the proximal end of the distal tip forms a lap joint with the distal end of the elongate shaft.

19. An intravascular catheter as in claim 18, wherein an inner diameter of the elongate shaft is equal to an inner diameter of the distal tip across the lap joint.

20. An intravascular catheter as in claim 19, wherein an outer diameter of the elongate shaft is equal to an outer diameter of the distal tip across the lap joint.

21. An intravascular catheter as in claim 12, wherein the intermediate layer of the distal tip comprises more than 70% radiopaque agent.

22. An intravascular catheter as in claim wherein 12, the radiopaque agent is homogeneously distributed throughout the polymer of the inner layer.

23. An intravascular catheter as in claim 12, wherein the radiopaque agent is admixed with the polymer of the inner layer.

24. An intravascular catheter, comprising:

an elongate shaft having a proximal end, a distal end and a lumen extending therethrough, the elongate shaft having a length and an outside diameter suitable for intravascular navigation; and a distal tip having a proximal end, a distal end and a lumen extending therethrough, the proximal end of the tip connected to the distal end of the elongate shaft, the distal end of the tip defining a terminal end of the catheter, wherein the distal tip includes an intermediate layer having a lap joint connection between the elongate shaft and the distal tip, comprising a polymer loaded with a radiopaque agent disposed between inner and outer polymeric layers.

25. An intravascular catheter, comprising:

an elongate shaft having a proximal end, a distal end and a lumen extending therethrough, the elongate shaft having a length and an outside diameter suitable for intravascular navigation; and a distal tip having a proximal end, a distal end and a lumen extending therethrough, the proximal end of the tip connected to the distal end of the elongate shaft, the distal end of the tip defining a terminal end of the catheter, wherein the distal tip includes an intermediate layer comprising a polymer loaded with a radiopaque agent disposed between inner and outer polymeric layers, wherein the polymer of the inner, intermediate and outer layers is the same and is readily bondable, wherein the inner and outer polymeric layers increase bond strength between the intermediate layer and the distal end of the elongate shaft.

* * * * *

UNITED STATES PATENT AND TRADEMARK OFFICE
CERTIFICATE OF CORRECTION

PATENT NO. : 6,652,507 B2
DATED : November 25, 2003
INVENTOR(S) : Henry J. Pepin It is certified that error appears in the above-identified patent and that said Letters Patent is hereby corrected as shown below:

Column 5,
Line 9, before "agent", insert -- radiopaque --.
Line 11, after "outer" and before "to", insert -- layers extend --.
Line 13, after "shaft" and before "polymer", insert -- comprises a --.
Line 30, delete "wherein 12,", and insert therefor -- 12, wherein --.

Signed and Sealed this

Sixth Day of July, 2004

JON W. DUDAS
*Acting Director of the United States Patent and Trademark Office*